US012350085B2

(12) United States Patent
Ledan et al.

(10) Patent No.: US 12,350,085 B2
(45) Date of Patent: Jul. 8, 2025

(54) MAMMOGRAPHY IMAGING SYSTEM WITH UNIVERSAL ATTACHMENT STRUCTURES

(71) Applicant: GE Precision Healthcare LLC, Wauwatosa, WI (US)

(72) Inventors: Mathieu Ledan, Saint Cyr l'École (FR); Renaud Lecoeur, Chamboi (FR); Ayoub Denguir, Chaville (FR)

(73) Assignee: GE Healthcare, Waukesha, WI (US)

( * ) Notice: Subject to any disclaimer, the term of this patent is extended or adjusted under 35 U.S.C. 154(b) by 333 days.

(21) Appl. No.: 18/110,062

(22) Filed: Feb. 15, 2023

(65) Prior Publication Data

US 2024/0268775 A1 Aug. 15, 2024

(51) Int. Cl.
*A61B 6/00* (2024.01)
*A61B 6/04* (2006.01)
*A61B 6/50* (2024.01)
*A61B 6/46* (2024.01)

(52) U.S. Cl.
CPC ............ *A61B 6/502* (2013.01); *A61B 6/0414* (2013.01); *A61B 6/4435* (2013.01); *A61B 6/54* (2013.01); *A61B 6/461* (2013.01); *A61B 6/467* (2013.01)

(58) Field of Classification Search
CPC . A61B 1/00039; A61B 1/00042; A61B 6/032; A61B 6/04; A61B 6/0407; A61B 6/46; A61B 6/502; A61B 6/548; A61B 6/54; A61B 6/025; A61N 5/1049; A61N 2005/1061; A61N 2005/1062
See application file for complete search history.

(56) References Cited

U.S. PATENT DOCUMENTS

| 8,175,219 | B2 | 5/2012 | Defreitas et al. |
| 9,659,369 | B2 | 5/2017 | Nakayama et al. |
| 10,874,366 | B2 | 12/2020 | Dueppenbecker et al. |
| 2012/0020464 | A1 | 1/2012 | Matsuura |
| 2016/0183898 | A1 | 6/2016 | Cormican |

(Continued)

FOREIGN PATENT DOCUMENTS

JP 2009082399 A 4/2009

OTHER PUBLICATIONS

EP application 24154213.3 filed Jan. 26, 2024—extended Search Report issued Jun. 18, 2024; 22 pages.

(Continued)

*Primary Examiner* — Don K Wong
(74) *Attorney, Agent, or Firm* — Boyle Frederickson, S.C.

(57) ABSTRACT

According to one aspect of an exemplary embodiment of the disclosure, an imaging device or system, e.g., a mammography imaging system or device, includes a detector fixed on the device and a radiation source spaced from the detector. The device further includes a number of support structures moveably disposed on the device in positions between the detector and the radiation source. The support structures include attachment structures thereon that are each adapted to engage one or more components of the imaging device for use therewith, including but not limited to a compression paddle, a magstand and a positioned including a biopsy device thereon. The support structures can be engaged with any of the components in order to simplify the manner of attachment of the components to the device and to enable the components to readily be attached to the device in a variety of configurations.

20 Claims, 8 Drawing Sheets

(56) References Cited

U.S. PATENT DOCUMENTS

| | | |
|---|---|---|
| 2019/0216412 A1 | 7/2019 | Vartolone |
| 2020/0060632 A1 | 2/2020 | Blaski et al. |
| 2020/0253568 A1 | 8/2020 | Hong |
| 2021/0186450 A1* | 6/2021 | Vancamberg .......... A61B 6/584 |

OTHER PUBLICATIONS

JP2009-082399 English Abstract; Espacenet.com Sep. 13, 2024; 1 page.

* cited by examiner

MAMMOGRAPHY IMAGING SYSTEM WITH UNIVERSAL ATTACHMENT STRUCTURES

FIELD OF THE DISCLOSURE

The present disclosure relates generally to medical imaging systems, including mammography systems and devices, and more specifically to component attachment structures for mammography systems.

BACKGROUND OF THE DISCLOSURE

Embodiments of the invention relate generally to X-ray medical imaging, and more particularly to devices, systems and methods employed to perform various imaging procedures, such as mammography imaging procedures including but not limited to spectral mammography (SM), such as 2D/3D dual-energy contrast-enhanced (CE) mammography exams, full-field digital mammography (FFDM) or digital breast tomosynthesis (DBT) mammography exams.

Spectral mammography (SM) is an X-ray imaging modality used to scan breasts for screening, diagnosis and/or interventional examinations. The effectiveness of spectral mammography is affected by numerous factors, one of which is the two-dimensional (2D) rendering of images obtained using SM.

Alternative systems to SM are also known for breast imaging. Some examples include full-field digital mammography, which captures the image directly onto a flat-panel detector, computed radiography, which involves the use of a cassette that contains an imaging plate, or digital breast tomosynthesis (DBT). A digital breast tomosynthesis (DBT) or mammography-tomography (mammo-tomo) system is a dedicated mammography system that acquires several (e.g., tens of) angularly offset projection X-ray images and uses the resulting X-ray image data to reconstruct three-dimensional (3D) image datasets.

The 3D image datasets are used to form various volumetric representations of the imaged breast, including an entire 3D volume of the breast, and various 3D sections of the 3D volume, such as slices or slabs constituting specified thicknesses of the 3D volume oriented to provide the desired view of one or more regions of interest (ROI) detected within the 3D image dataset.

In addition, when the 3D image datasets of the breast have been produced, after being utilized in a suitable diagnosis procedure, they can be utilized to guide a biopsy device employed with the DBT system into the breast to obtain a biopsy of the region of interest (ROI) identified within the 3D image datasets. In DBT systems, the biopsy device is disposed directly on the DBT system in order to be able to perform the biopsy utilizing the 3D image dataset or to use a stereo-pair of camera images of the breast and biopsy device with a subsequent triangulation of the biopsy device to the ROI in the breast to guide the biopsy device to the ROI.

With regard to the use of these DBT mammography systems, the set-up of the system to obtain the images requires the attachment of various devices to the system in order to provide the system with the proper positioning, i.e., compression, of the breast to obtain the image quality desired. In mammography systems, the devices that are attached to the system to perform the imaging and/or biopsy procedure include a compression paddle, a magnification device, and/or a biopsy holder, which is utilized to locate the biopsy device on the mammography system in a location where the biopsy device can perform the desired biopsy procedure under the guidance of the mammography system. When the mammography imaging system is operated in a screening configuration, the compression paddle, and optionally the magnification device or magstand, are connected to the system. Conversely, when the imaging system is employed in a diagnostic configuration, the biopsy positioner or holder and a compression paddle compatible with the operation of the biopsy device on the biopsy holder are secured to the imaging system. In both configurations, the detector is fixed as a part of the imaging system, with the bucky secured to the detector to provide a suitable x-ray transparent breast support surface along with the image enhancing, anti-scatter grid located within the bucky.

In many prior art diagnostic mammography imaging devices, such that disclosed in US Patent Application Publication No. US20200060632, entitled *Apparatus And Method For Mammographic Breast Compression*, the entirety of which is expressly incorporated herein by reference for all purposes, the mammography system includes a number of dedicated attachment structures positioned thereon. First, with reference to the prior art mammography system illustrated generally at 1010 in FIG. 1A, the mammography system 1010 includes a detector attachment structure 1012 for engaging the detector 1018 to the mammography system 1010. The detector attachment structure 1012 is connected to the gantry 1016 of the mammography system 1010 to provide a fixed and permanent location for the position of the detector 1018 on the mammography system 1010. Further, the detector 1018 can include a bucky 1014 secured directly over the top of the detector 1018 for the mammography system 1010, or in the form of a removable cassette (not shown) or in the form of an integral component of the detector 1018. In any of these configurations for the bucky 1014 on the detector 1018, the detector attachment structure 1012 requires suitable selectively disconnectable electronic connections that can be engaged with the bucky 1014 to enable signals to be transmitted to and from the bucky 1014 to the mammography system 1010 via the bucky attachment structure 1012 for the operation for the bucky 1014.

Figure 1A:
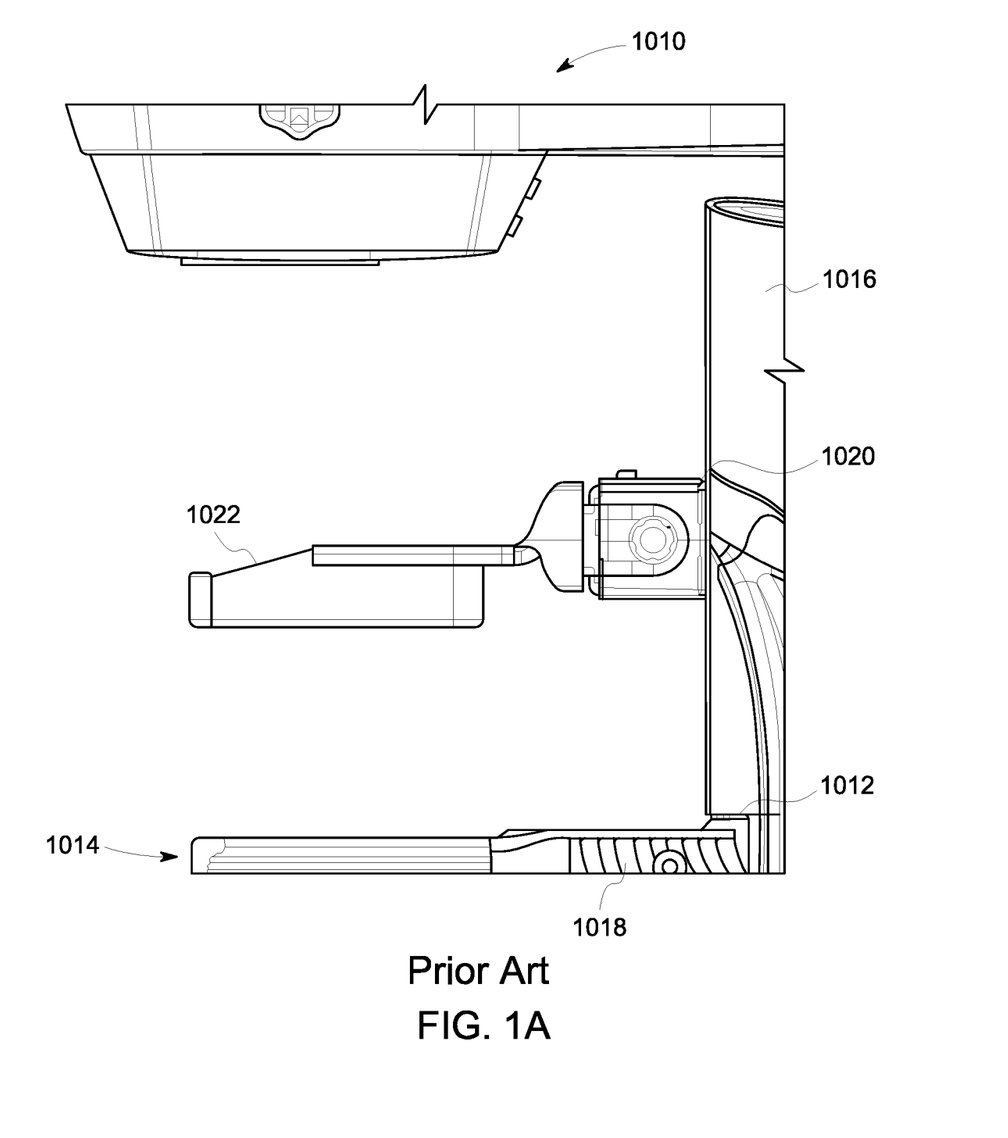
FIGS. 1A, 1B and 1C are an isometric views of a prior art mammography imaging system.

The mammography system 1010 also includes a paddle attachment structure 1020 disposed on the gantry 1016 above the bucky attachment structure 1012. The paddle attachment structure 1020 provides an attachment point for a compression paddle 1022 on the mammography system 1010. The paddle attachment structure 1020 is vertically moveable with regard to the gantry 1016 in order to enable the paddle 1022 to be moved towards the detector 1018 and the bucky 1014 to provide the required compression to the breast positioned on the detector 1018/bucky 1014 to achieve the desired quality for the images of the breast, i.e., to achieve a uniform thickness to the breast to get a uniform contrast and also to keep the breast in place avoiding blur. The paddle attachment structure 1020 allows the paddle 1022 to be readily switched and/or replaced on the paddle attachment structure 1020 such that the paddle 1022 best suited for use with a particular patient can be quickly and easily secured to the paddle attachment structure 1020. The paddle attachment structure 1020 may also include various features and/or mechanisms therein, such as a motorized paddle shift mechanism that enables the paddle attachment structure 1020 to shift the position of the paddle 1022 on the paddle attachment structure 1020 to better position the paddle 1022 for the imaging procedure to be performed.

Figure 1B:
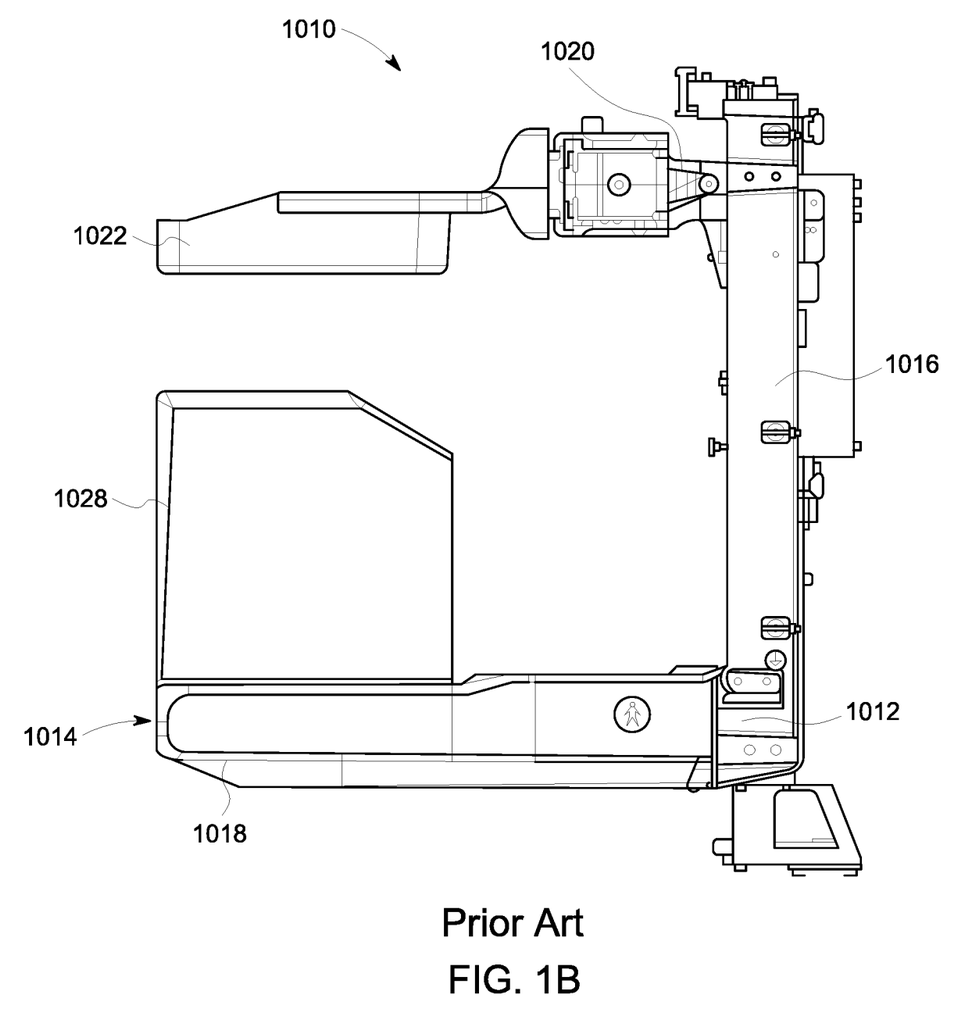
Figure 1C:
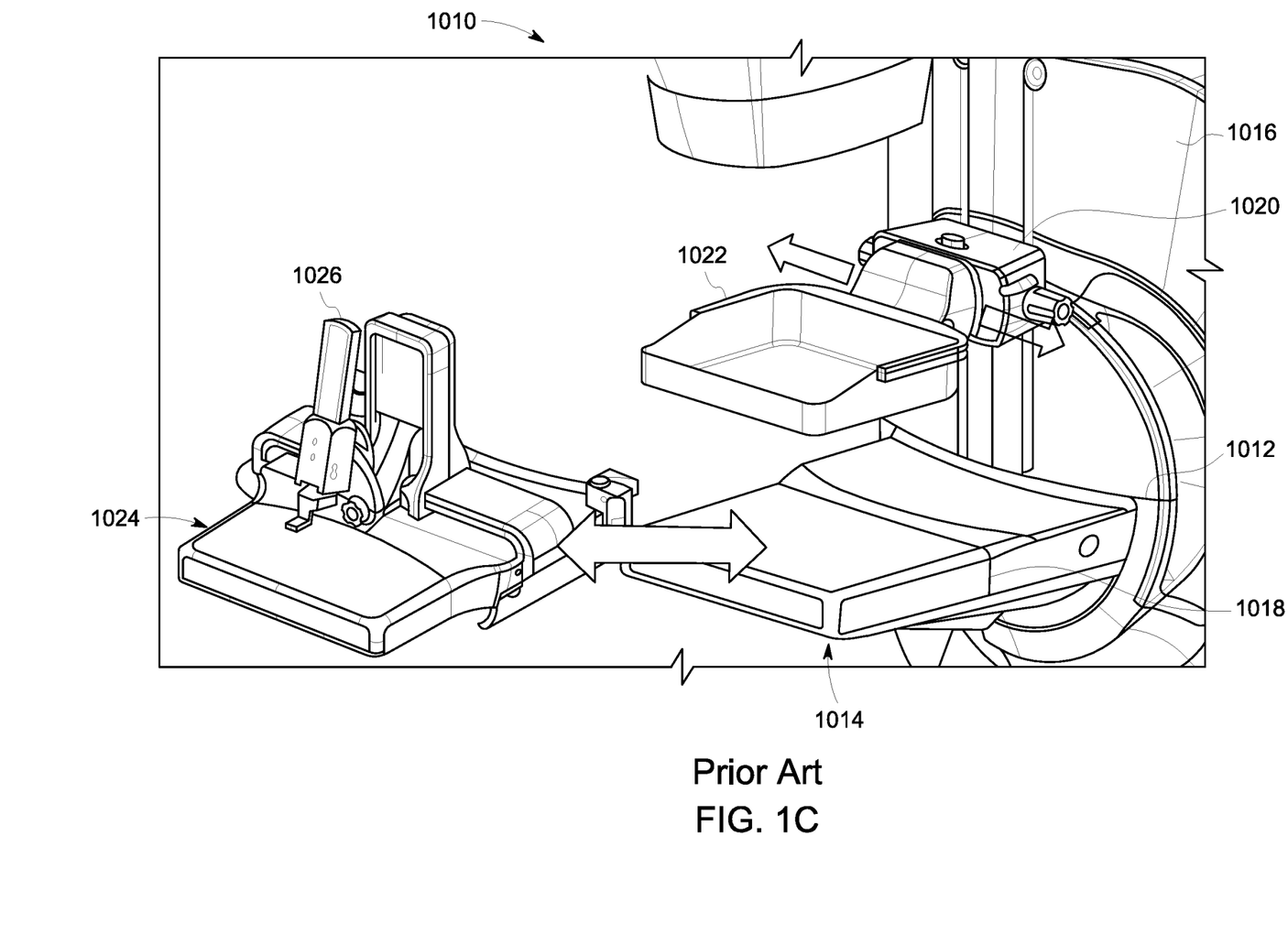

When performing a biopsy procedure, as shown in FIG. 1C, the bucky 1014 can be disengaged from the detector 1018 to enable a biopsy positioner 1024 to be secured to the detector 1018. The biopsy positioner 1024 replaces the bucky 1014, such that in addition to supporting the biopsy device 1026 thereon for use in the biopsy procedure, the biopsy positioner 1024 provides the breast support surface on the detector 1018 and the anti-scatter grid for any images obtained with the biopsy positioner 1024 on the detector 1018 during the biopsy procedure.

Finally, as illustrated in FIG. 1B, when it is desired to obtain a magnified image of the breast, where the breast needs to be positioned closer to the X-ray source, a magstand 1028 can be secured to the bucky 1014 or detector 1018 to provide the desired magnification factor for the images. To be able to produce the desired images, the magstand 1028 is formed with a cube-like, X-ray transparent structure that is positioned on/secured to the breast support surface of the bucky 1014 or the detector 1018 in order to elevate the location of the breast positioned thereon to a height that provides the desired magnification of the breast.

While the bucky 1014 or biopsy positioner 1024 can be interchangeably attached to the detector 1018, and the paddle 1022 can be switched on the paddle attachment structure 1020, for the desired operation of the mammography system 10, the dedicated attachment structures 1012 and 1020 functionally limit the ease of operation of the mammography system 1010. Further, the requirement of the separate bucky 1014 for each of the detector 1018 and the biopsy positioner 1024 greatly increases the cost and complexity of these components of the mammography system 1010.

Therefore, with regard to the aforementioned shortcomings of prior art mammography imaging systems concerning the attachment structures for the components utilized with the mammography systems, it is desirable to develop an improved mammography system and attachment structures with an associated method for securing the required components thereto for the operation of the of the mammography system with or without a biopsy device.

SUMMARY OF THE DISCLOSURE

According to one aspect of an exemplary embodiment of the present disclosure, a mammography system includes a gantry having, a radiation source, a detector fixed to the gantry and alignable with the radiation source and defining a compression surface, a first support structure moveably disposed on the gantry between the radiation source and the detector and a second support structure moveably disposed on the gantry between the radiation source and the detector, a controller operably connected to the gantry to control the operation of the radiation source and detector to generate image data, the controller including a central processing unit and interconnected electronic memory unit for processing the image data from the detector, a display operably connected to the controller for presenting information to a user, and a user interface operably connected to the controller to enable user input to the controller, wherein the first support structure and the second support structure each include identical component attachment structures thereon.

According to still another aspect of an exemplary embodiment of the present disclosure, an imaging system includes a gantry having a radiation source, a detector alignable with the radiation source and defining a compression surface, a first support structure moveably disposed on the gantry between the radiation source and the detector, and a second support structure moveably disposed on the gantry between the radiation source and the detector, a controller operably connected to the gantry to control the operation of the radiation source and detector to generate image data, the controller including a central processing unit and interconnected electronic memory unit for processing the image data from the detector, a display operably connected to the controller for presenting information to a user, and a user interface operably connected to the controller to enable user input to the controller, wherein the first support structure and the second support structure each include a component attachment structure thereon.

According to still another aspect of an exemplary embodiment of the present disclosure, a method for performing an imaging procedure on an imaging system, the includes the steps of providing an imaging system having a gantry including a radiation source, a detector fixed to the gantry and alignable with the radiation source and defining a compression surface, a first support structure moveably disposed on the gantry to move along a compression axis between the radiation source and the detector and including a first component attachment structure, and a second support structure moveably disposed on the gantry to move along a compression axis between the radiation source and the detector and including a second component attachment structure identical to the first component attachment structure, a controller operably connected to the gantry to control the operation of the radiation source and detector to generate image data, and to control the movement of the first support structure and the second support structure, the controller including a central processing unit and interconnected electronic memory unit for processing the image data from the detector, a display operably connected to the controller for presenting information to a user and a user interface operably connected to the controller to enable user input to the controller, engaging a first component with one of the first support structure or the second support structure, moving the first component along the compression axis between the radiation source and the detector, and operating the radiation source and detector to perform a procedure with the imaging system.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Further, while the embodiments disclosed herein are described with respect to a mammography apparatus for the 2-dimensional imaging of breast tissue, it is to be understood that embodiments of the invention may be applicable to other types of imaging devices for both 2-dimensional and 3-dimensional imaging including, for example, fluoroscopy, full-filed digital mammography, digital breast tomosynthesis (DBT) and spectral mammography (single or multi-energy), as well as for imaging procedures for tissue other than breast tissue. Further still, embodiments of the invention may be used to analyze tissue, generally, and are not limited to analyzing human tissue.

Figure 2:
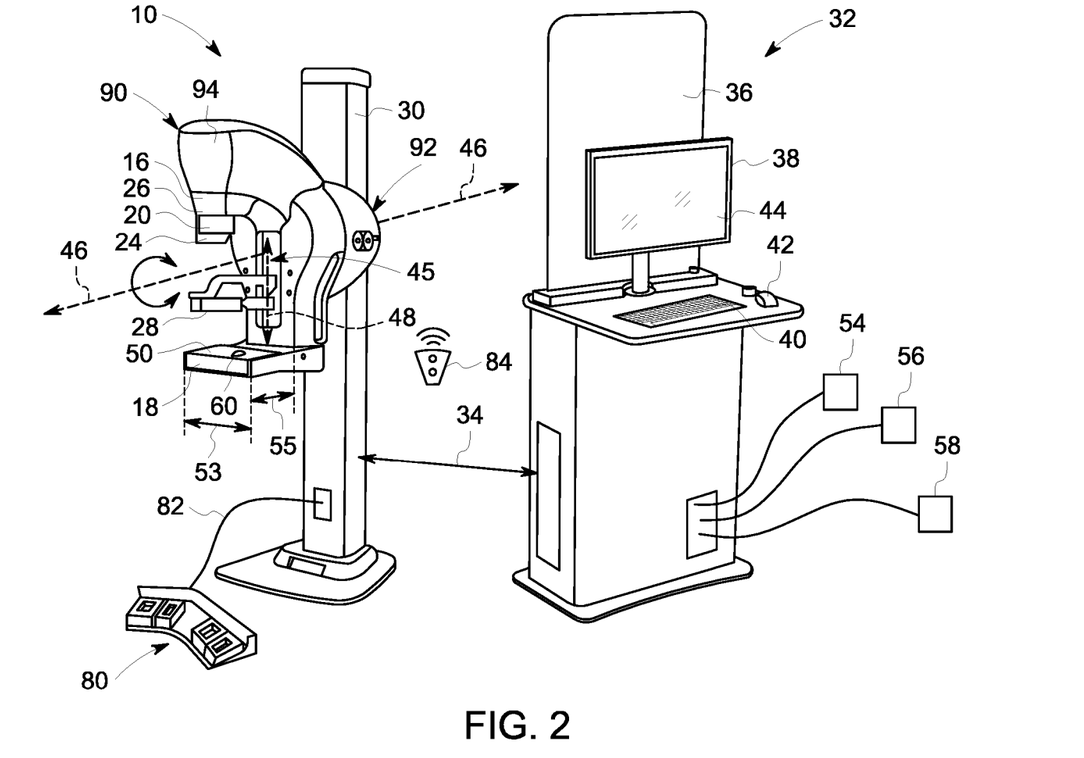
FIG. 2 is a perspective view of an imaging device in the form of a mammography apparatus for imaging the breast tissue of a patient, in accordance with an embodiment of the disclosure.
Figure 3:
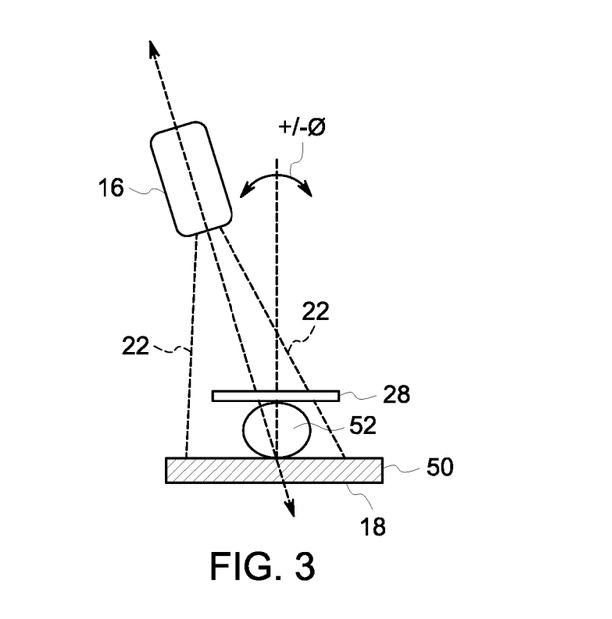
FIG. 3 is a diagram of the system of FIG. 2, showing the radiation source of the system in a scanning position, in accordance with an embodiment of the disclosure.

Referring now to FIGS. 2 and 3, the major components of an exemplary imaging system 10 formed as a mammography system 12 for imaging breast tissue according to an embodiment of the invention are shown. The system 10, such that disclosed in US Patent Application Publication No. US20200060632, entitled Apparatus And Method For Mammographic Breast Compression, the entirety of which is expressly incorporated herein by reference for all purposes, includes a radiation source/x-ray source 16, a radiation detector 18, and a collimator 20. The radiation source 16 is movable between a variety of imaging positions relative to the detector 18, and is operative to emit radiation rays 22 (FIG. 3) that are received by the radiation detector 18 to provide an image of an object, such as a breast 52. In embodiments, the system 10 may include a patient shield 24 mounted to the radiation source 16 via face shield rails 26 to prevent the patient's head from obstructing the radiation rays and protecting the patient from the radiation rays 22.

Referring still further to FIGS. 2 and 3, the system 10 also includes a compression paddle or plate 28 and a support structure 30 to which one or more of the radiation source 16, radiation detector 18, and/or compression plate 28 are mounted. In embodiments, the system 10 may further include a controller 32. The controller 32 may be a workstation having at least one processor/central processing unit/computer and a memory device/database that stores information and/or instructions for the operation of the system 10 that are employed by the controller 32, as shown in FIG. 1 or, in other embodiments, the controller 32 may be embedded/integrated into one or more of the various components of the system 10 disclosed above. In embodiments, the controller 32 may be in electrical communication with the radiation source 16, radiation detector 18, and/or the compression plate 28 via a cable 34. As will be appreciated, in embodiments, the connection 34 may be a wireless connection. In embodiments, the controller 32 may include a radiation shield 36 that protects an operator of the system 10 from the radiation rays 22 emitted by the radiation source 16. The controller 32 may further include a display 38, a keyboard 40, mouse 42, and/or other appropriate user input devices that facilitate control of the system 10 via a user interface 44.

As further shown in FIGS. 2 and 3, the radiation source 16, along with the radiation detector 18, forms part of an x-ray system which provides x-ray imagery for the purpose of imaging a body part of a patient, such as breast 52. As stated above, the radiation source 16 emits the radiation rays 22 such that the radiation rays 22 travel from the radiation source 16 to the radiation detector 18. While the radiation rays 22 are discussed herein as being x-rays, it is to be understood that the radiation source 16 may emit other types of electromagnetic rays which can be used to image a patient. The radiation source 16 may be mounted to the support structure 30 such that the radiation source can rotate around an axis 46 in relation to the radiation detector 18, although movement of the radiation source 16 in paths other than rotation about a fixed axis, such as during digital breast tomosynthesis (DBT), are also envisioned. In embodiments, the radiation detector 18 may be configured to rotate or translate within its housing, such as in the directions indicated by arrows 53 and 55.

In the illustrated exemplary embodiment of FIG. 2 the radiation source 16 and the detector 18 are mounted to a gantry 90 that is secured to the support structure 30. The support structure 30 houses a translation mechanism 92 that is operably connected to the gantry 90. The translation mechanism 92 is operable to move the gantry 90 vertically with respect to the support structure 30 in order to position the gantry 90 at the appropriate height to accommodate the dimensions of the patient on which the system 10 is being utilized. The translation mechanism 92 is also operable to rotate the gantry 90 relative to the support structure 30 about the horizontal axis 46 in order to position the gantry 90 rotationally with regard to the patient, as necessary.

The gantry 90 includes a generally C-shaped body 94 with the radiation source 16 at one end and the detector 18 at the opposite end. In this configuration, regardless of the vertical and/or rotational orientation of the gantry 90, such as to position the radiation source 16 and detector 18 relative to the patient breast 52 to obtain x-ray images at various orientations, such as for craniocaudal (CC) or mediolateral oblique (MLO) views, among others, the radiation source 16 is disposed in alignment with the detector 18. In this position, the detector 18 is capable of receiving the x-rays 22 emitted from the radiation source 16 that pass through the portion of the patient, i.e., patient breast 52, located between the radiation source 16 and the detector 18 in order to generate image data for transmission to the control system 32 of the mammography device/system 10 to create/reconstruct a 3D image dataset for viewing by a physician, such as by using DBT, among other known methods.

Additionally, in another embodiment the radiation source 16 can be attached to the gantry 90 to rotate and/or move independently of the gantry 90 and detector 18 in order to enable the radiation source 16 to take x-ray images of the patient breast at various angles relative to the detector 18, e.g., between +/−60°. The images obtained between these angles for the radiation source 16 can be used either for creation of stereoscopic images in a biopsy procedure using the system 10 or for DBT when operating the system 10 in an imaging mode.

As stated above, the radiation detector 18 receives the radiation rays 22 emitted by the radiation source 16. In embodiments, data regarding the radiation rays 22 received by the radiation detector 18 may be electrically communicated to the controller 32 from the radiation detector 18 via cable/electronic connection 34 such that the controller 32 generates one or more images which may be shown on the display 38 and stored in the memory device.

The compression plate 28 is operative, in response to instruction from the controller 32 or in response to instructions from controller(s) on or near the mammography system 10, such as remote control, 84, or switch controllers 80 connected by cable 82, to move towards and away from the radiation detector 18 as indicated by arrows/compression axis 48 such that the compression plate 28 flattens and holds a body part, e.g., breast 52, in place against the surface 50 of the radiation detector 18. In this respect, the radiation detector 18 and the surface 50 thereof is referred to herein as a "compression surface or support plate" that cooperates with the compression plate 28 to compress and clamp a breast of a patient therebetween.

Figure 4:
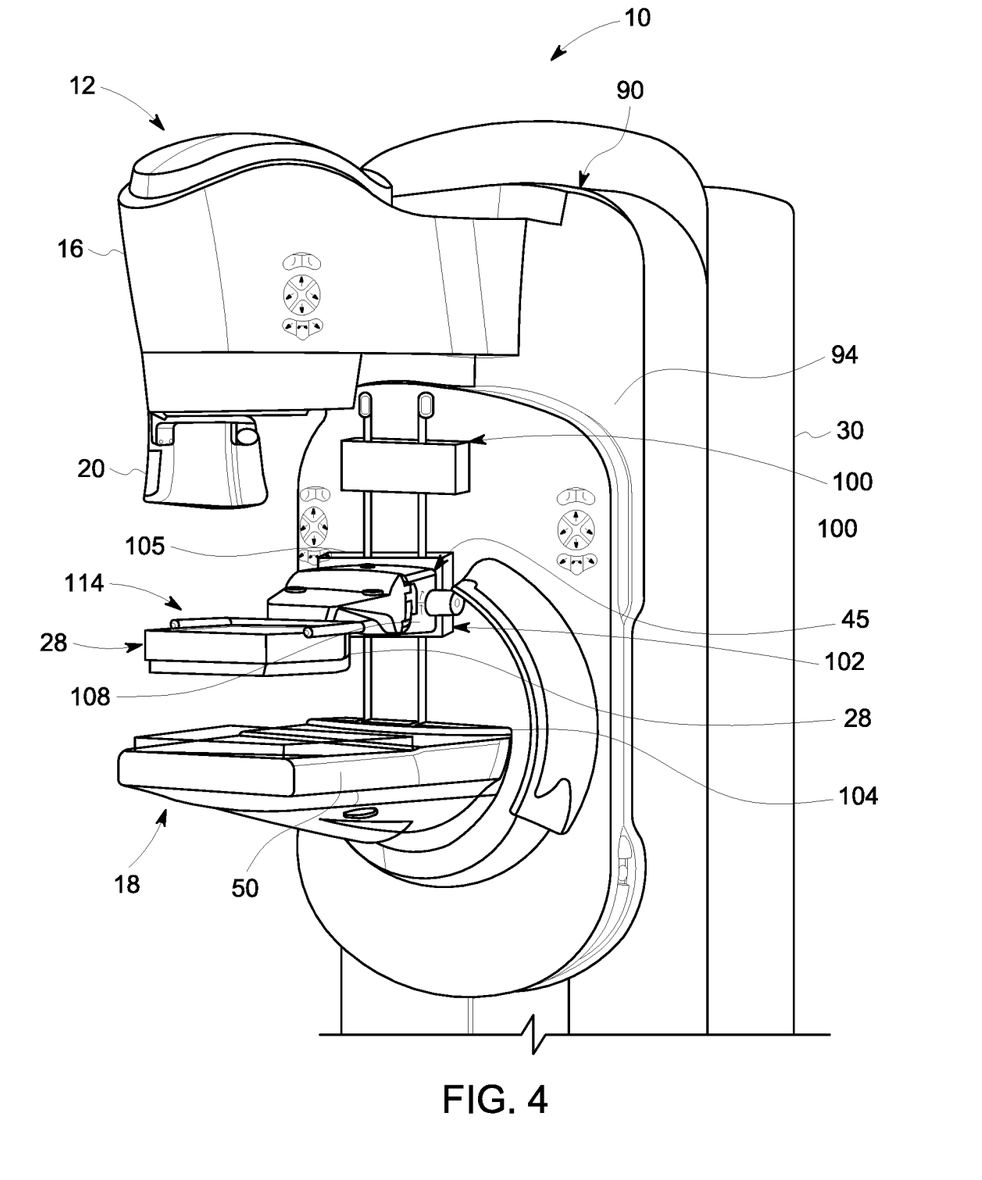
FIG. 4 is an isometric view of the mammography system of FIG. 2 including a first embodiment of first and second component support structures thereon in accordance with an embodiment of the disclosure.

In one exemplary embodiment illustrated in FIG. 4, the gantry 90 includes a first support structure 100 and a second support structure 102 each of which are operably connected to a compression axis movement mechanism 45 located on and/or within the gantry 90 that is able to move each of the first support structure 100 and the second support structure 102 relative to the gantry 90 along the compression axis 48, e.g., vertically in the orientation of the gantry 90 shown in FIG. 4. The first support structure 100 and the second support structure 102 are independently connected to the movement mechanism 45, or to separate and aligned movement mechanisms 45, such as mechanisms 45 oriented in a side-by-side configuration within the gantry 90, such that each of the first support structure 100 and the second support structure 102 are separately moveable with regard to the gantry 90. The movement mechanism 45 is operable within the gantry 90 at any rotational or vertical position of the gantry 90 to move the first support structure 100 and/or the second support structure 102 in a line either towards or away from the detector 18/support plate. The movement mechanism 45 can have any of a number of different configurations, but in one exemplary embodiment takes the form of a compression screw mechanism that is operable to move a component 114 attached to one of the first support structure 100 and the second support structure 102 plate 28 into engagement with the patient breast 52 to exert a predetermined pressure/compression on the breast 52 to retain the breast 52 in a stationary position between the plate 28 and the detector 18/support plate during imaging and/or biopsy procedures.

Along with the first support structure 100 and the second support structure 102, the gantry 90 includes a detector support structure 104. The detector support structure 104 is disposed at a conventional location for the disposition of the radiation detector 18, or bucky, as in prior art mammography systems. However, the detector support structure 104 is constructed to be fixed with regard to the gantry 90 such that the detector 18 is also fixed to the gantry 90. Further, in one exemplary embodiment, the detector 18 can be fixed to the detector support structure 104, such that the detector 18 is not removable from the gantry 90 in normal operation of the mammography system 10.

With the detector 18 mounted in a non-releasable manner to the detector support structure 104, the first support structure 100 and the second support structure 102 are configured to include universal component attachment structures 106, such as any suitable mechanical, e.g., spring-biased pin, and/or electrical attachment structures, that allow the interconnection of various components of the mammography system 10 to each of the first support structure 100 and the second support structure 102. For example, the first support structure 100 and the second support structure 102 can each include both mechanical and electrical connections for any component 114 to be secured thereto in order to provide an interconnection that both mechanically holds and supports the component 114 on the first support structure 100 and the second support structure 102 and electrically connects the component 114 with the controller 32 to enable the controller 32 to provide any required power or control signals to the component 114 and to receive any data or feedback from the component 114 engaged with either of the first support structure 100 or the second support structure 102.

In one exemplary embodiment of the disclosure, the first and second support structures 100,102 can each include identical component attachment structures 106 that are complementary to attachment structures 108 disposed on each of the components 114, e.g., the compression paddle 28, a biopsy positioner 110 and a magstand 112, to be employed with the mammography system 10. As such, each of the components 114 including the complementary attachment structure 108, or that can be releasably attached to the associated complementary attachment structure 108, can be secured to the attachment structure 106 on either of first support structure 100 and the second support structure 102 to achieve an optimal configuration for the components 114 for the desired mode of operation of the mammography system 10. Further, each of the complementary attachment structures 108 on the components 114 includes an emergency release (not shown) to allow the disengagement of the complementary attachment structure 108 from the universal component attachment structure 106 in the event of a loss of power to the mammography system 10.

Figure 5:
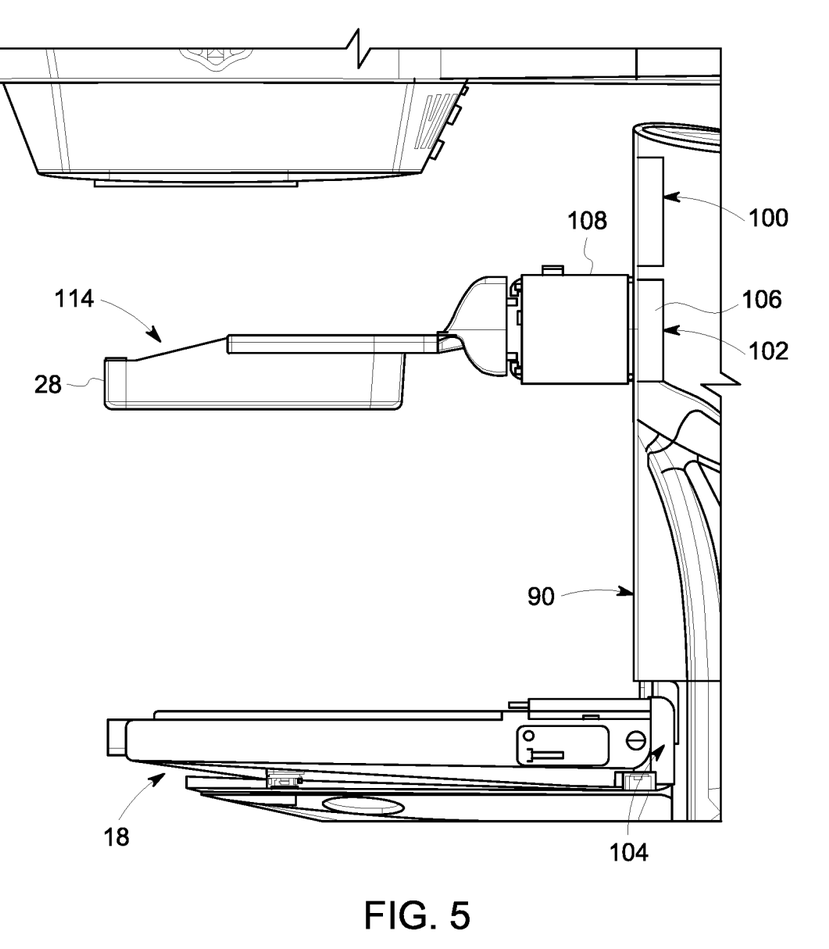
FIG. 5 is a side elevation view of another embodiment of the mammography system and of FIG. 4 in a first imaging configuration, in accordance with an embodiment of the disclosure.

Referring now to FIG. 5, in a first configuration for the mammography system 10, the compression paddle 28, which can be integrally formed with or releasably attachable to the complementary attachment structure 108 engageable with the component attachment structure 106 on the second support structure 102, is connected to the lower, second support structure 102, with the upper, first support structure 100 being unattached to a component 114. In this configuration, the paddle 28 can be moved vertically or along the compression axis 48 via the movement mechanism 45 to position the paddle 28 at the desired location for appropriate compression of the breast disposed between the paddle 28 and the detector 18, such as is desired during a conventional mammography imaging procedure performed by the mammography system 10, and to remove the compression and allow displacement of the breast 52 after completion of the diagnostic or screening imaging procedure. In addition, the complementary attachment structure 108 located on the paddle 28 can include a manual or motorized paddle shift mechanism (not shown) to enable adjustment of the paddle 28 in a lateral direction parallel to the detector surface 50.

Figure 6:
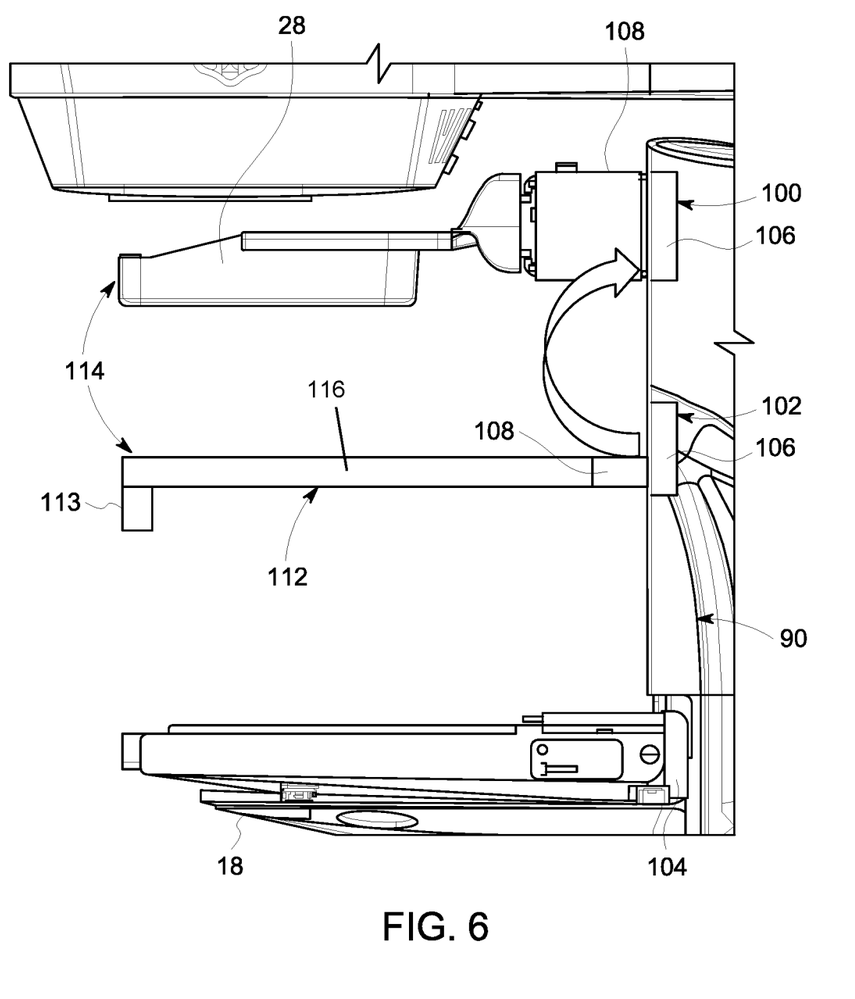
FIG. 6 is a side elevation view of another embodiment of the mammography system and of FIG. 4 in a second imaging configuration, in accordance with an embodiment of the disclosure.

Looking now at FIG. 6, in a second configuration for the mammography system 10, the compression paddle 28 can be attached to the first support structure 100 and the magstand attachment 112 can be secured to the second support structure 102. The magstand 112 is formed as a planar member 116 of an X-ray transparent material. As the vertical movement of the second support structure 102 enables the positioning of the magstand 112 where desired relative to the radiation source 16, the magstand 112 can be formed with a plate-like, or thin planar configuration with a significantly reduced thickness or height from the required cube-like structure of prior art magstands disposed on the detector 18. Further, the vertical movement of the magstand 112 via the movement mechanism 45 enables the magstand 112 to be positioned relative to the X-ray source 16 to achieve the desired factor of magnification for the images of the breast positioned on the magstand 112 and secured thereto by the complementary vertical movement of the paddle 28 secured to the first support structure 100 to compress the breast 52 between the paddle 28 and the magstand 112. This provides an amount of flexibility regarding the magnification of the images that is not possible with prior art mammography systems. Further, the magstand 112 can include a forward tab 113 disposed opposite the second support structure 102 the extends perpendicularly from the magstand 112, and in a direction towards the detector 18 as shown in FIG. 6. The forward tab 113 operates as a barrier to prevent any portion of the patient other than the breast 52 from being positioned within the field of view of the radiation source 16 and ensure the images obtained by the radiation rays 22 only contain the breast 52.

Figure 7:
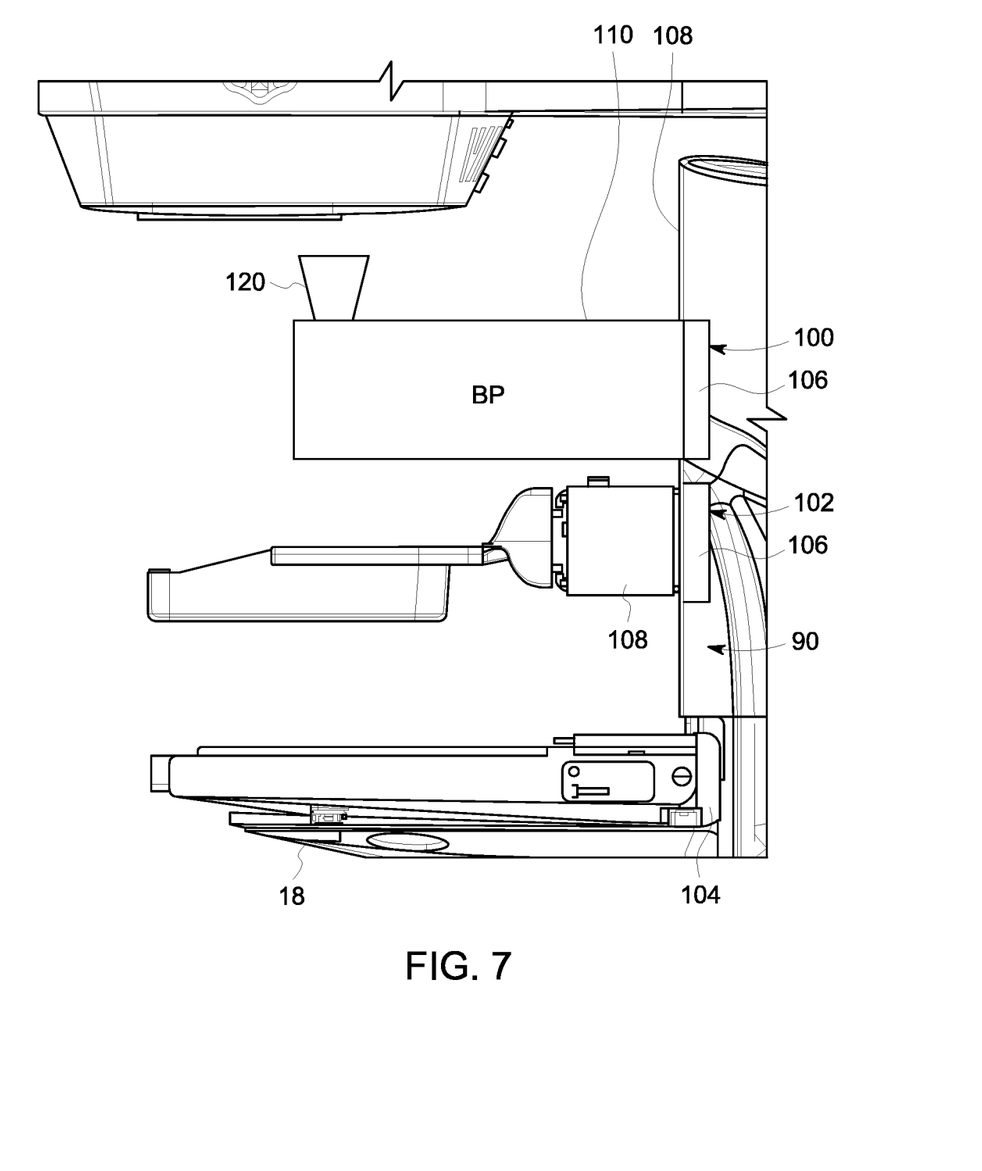
FIG. 7 is a side elevation view of another embodiment of the mammography system and of FIG. 4 in a biopsy imaging configuration, in accordance with an embodiment of the disclosure.

Looking now at FIG. 7, in a third configuration for the mammography system 10, the paddle 28 is attached to the second support structure 102, similar to the configuration of FIG. 5. However, the first support structure 100 is connected to a biopsy positioner 110. The biopsy positioner 110 includes a biopsy device 120 positioned thereon and operable by the control system 32 to perform a biopsy procedure. The biopsy positioner 110 can be formed to have degrees of freedom or motion in the 2-dimensional plane parallel to the surface 50 of the detector 18, thereby simplifying the construction of the biopsy positioner 110 and/or biopsy device 120 from prior art biopsy positioners requiring movement in three dimensions due to the inability of the biopsy positioner to move on the detector. This simplification is achieved due to the positioning of the biopsy positioner 110 on the first support structure 100, which is capable of providing the movement of the positioner 110 and the biopsy device 120 disposed thereon along the Z- or compression axis 48. Further, as the paddle 28 is attached to the second support structure 102 below the first support structure 100 and biopsy positioner 110, the movement of the paddle 28 to achieve the desired compression of the breast does not interfere with the movement of the movement of the positioner 110. More specifically, in one exemplary embodiment, the paddle 28 can be secured to the second support structure 102 and moved to compress the breast 52 between the paddle 28 and the detector surface 50 as desired. Subsequently, and optionally after the completion of a diagnostic imaging procedure of the compressed breast 52 using the mammography system 10, the biopsy positioner 110 can be attached to the first support structure 100 and moved into position by the movement mechanism 45 and the first support structure 100 to perform the biopsy procedure on the compressed breast 52, with the first support structure 100 moving the biopsy positioner 110 away from the paddle 28 and breast 52 after completion of the biopsy procedure. The second support structure 102 and the paddle 28 can also be moved away from the breast 52 to remove the compression of the breast 52 concurrently with or subsequently to the movement of the first support structure 100.

In all configurations of the components 114 attached to the first support structure 100 and the second support structure 102, because the detector 18 is disposed in a fixed position on the gantry 90 separate from the first support structure 100 and the second support structure 102, all components 114 can be simplified in their construction, e.g., with without the need for specialized attachment structure and/or a bucky and/or breast support surface thereon. Further, the movement of the first support structure 100 and the second support structure 102 via the movement mechanism(s) 45 can be independent of one another, allowing for precise control of the positioning of the components 114 secured to each of the first support structure 100 and the second support structure 102 in any desired configuration on the gantry 90.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A mammography system comprising:
 a. a gantry comprising:
  i. a radiation source;
  ii. a detector alignable with the radiation source and defining a compression surface;
  iii. a first support structure moveably disposed on the gantry between the radiation source and the detector; and
  iv. a second support structure moveably disposed on the gantry between the radiation source and the detector;
 b. a controller operably connected to the gantry to control the operation of the radiation source and detector to generate image data, the controller including a central processing unit and interconnected electronic memory unit for processing the image data from the detector,
 c. a display operably connected to the controller for presenting information to a user; and
 d. a user interface operably connected to the controller to enable user input to the controller,
 wherein the first support structure and the second support structure each include a component attachment structure thereon.

2. The mammography system of claim 1, wherein the component attachment structure on the first support structure and on the second support structure are identical.

3. The mammography system of claim 2, wherein each component attachment structure includes at least one of a mechanical connection, an electrical connection, and combinations thereof.

4. The mammography system of claim 1, wherein the first support structure and the second support structure are each moveable along a compression axis defined between the radiation source and the detector.

5. The mammography system of claim 4, wherein the first support structure and the second support structure are each independently moveable along the compression axis.

6. The mammography system of claim 1, wherein the component is a compression paddle.

7. The mammography system of claim 1, wherein the component is a magstand.

8. The mammography system of claim 7, wherein the magstand is formed with a planar configuration.

9. The mammography system of claim 7, wherein the magstand is formed with a forward tab at one end.

10. The mammography system of claim 1, wherein the component is a biopsy positioner.

11. The mammography system of claim 10, wherein the biopsy positioner includes a biopsy device exclusively moveable in directions parallel to the compression surface of the detector.

12. The mammography system of claim 1, wherein the first support structure and the second support structure are each connected to a movement mechanism disposed within the gantry.

13. The mammography system of claim 12, wherein the first support structure and the second support structure are independently moveable with respect to the gantry.

14. An imaging system comprising:
 a. a gantry comprising:
  i. a radiation source;
  ii. a detector fixed to the gantry and alignable with the radiation source and defining a compression surface;
  iii. a first support structure moveably disposed on the gantry between the radiation source and the detector; and
  iv. a second support structure moveably disposed on the gantry between the radiation source and the detector;
 b. a controller operably connected to the gantry to control the operation of the radiation source and detector to generate image data, the controller including a central processing unit and interconnected electronic memory unit for processing the image data from the detector,
 c. a display operably connected to the controller for presenting information to a user; and
 d. a user interface operably connected to the controller to enable user input to the controller,
 wherein the first support structure and the second support structure each include identical component attachment structures thereon.

15. The imaging system of claim 14, wherein the imaging system is a mammography system and further comprising at least one component including a complementary attachment structure and selected from a paddle, a magstand, a biopsy positioner and combinations thereof.

16. A method for performing an imaging procedure on an imaging system, the method comprising the steps of:
 a. providing an imaging system comprising:
  i. a gantry comprising:
   i. a radiation source;
   ii. a detector fixed to the gantry and alignable with the radiation source and defining a compression surface;
   iii. a first support structure moveably disposed on the gantry to move along a compression axis between the radiation source and the detector and including a first component attachment structure; and
   iv. a second support structure moveably disposed on the gantry to move along a compression axis between the radiation source and the detector and including a second component attachment structure identical to the first component attachment structure;
  ii. a controller operably connected to the gantry to control the operation of the radiation source and detector to generate image data, and to control the movement of the first support structure and the second support structure, the controller including a central processing unit and interconnected electronic memory unit for processing the image data from the detector,
  iii. a display operably connected to the controller for presenting information to a user; and
  iv. a user interface operably connected to the controller to enable user input to the controller;
 b. engaging a first component with one of the first support structure or the second support structure;
 c. moving the first component along the compression axis between the radiation source and the detector; and
 d. operating the radiation source and detector to perform a procedure with the imaging system.

17. The method of claim 16, further comprising the steps of:
 a. engaging a second component with the other of the first support structure or the second support structure;
 b. moving the second component along the compression axis between the radiation source and the detector.

18. The method of claim 16, wherein the first support structure and the second support structure are independently moveable along the compression axis.

19. The method of claim 16, wherein the first component is selected from a group consisting of a compression paddle, a magstand and a biopsy positioner.

20. The method of claim 19, wherein the biopsy positioner comprises a biopsy device exclusively moveable in directions parallel to the compression surface of the detector.

* * * * *